United States Patent [19]

Johnson et al.

[11] Patent Number: 4,811,599

[45] Date of Patent: Mar. 14, 1989

[54] BOREHOLE SAMPLING

[76] Inventors: Richard L. Johnson, 19600 N.W. Von Neumann Dr., Beaverton, Oreg. 97006-1999; John A. Cherry, 26 Academy Crescent, Waterloo, Ontario, N2L 5H7, Canada; James F. Pankow, 19600 N.W. Von Neumann Dr., Beaverton, Oreg. 97006-1999

[21] Appl. No.: 919,489

[22] Filed: Oct. 16, 1986

[30] Foreign Application Priority Data

Oct. 21, 1985 [CA] Canada ................................ 493411

[51] Int. Cl.⁴ ............................................. E21B 49/08
[52] U.S. Cl. .................................... 73/155; 73/864.15
[58] Field of Search ........... 73/864.63, 864.15, 864.11, 73/155, 863.23, 863; 166/264

[56] References Cited

U.S. PATENT DOCUMENTS 3,010,583  11/1961  Kenyon .................. 73/863.23 X
3,455,904  7/1969   Hopkin .................. 73/864.63 X
3,618,394  11/1971  Penton .................. 73/864.63 X Primary Examiner—Jerry W. Myracle
Attorney, Agent, or Firm—Anthony & Co. Asquith

[57] ABSTRACT

The disclosed sampler comprises a reservoir formed as a stainless steel tube of narrow diameter. Two copper tubes are attached to the reservoir, one each end, and the copper tubes may be crimped so as to seal the sample within the reservoir. The sample (of water) is allowed into the reservoir through a check-valve which is opened and closed by controlling the pressure—from the surface —inside the sampler. The disclosed sampler is sealed into the borehole by means of an inflatable collar, which is also under the control of a surface-manipulated pressure. Samples transported and stored in the sampler are presented for analysis complete with contained gases and uncontaminated.

15 Claims, 2 Drawing Sheets

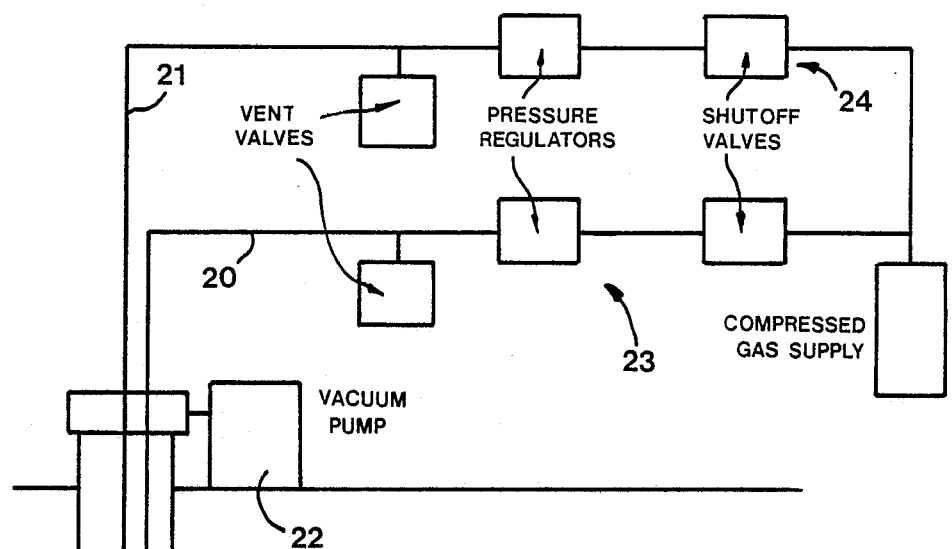
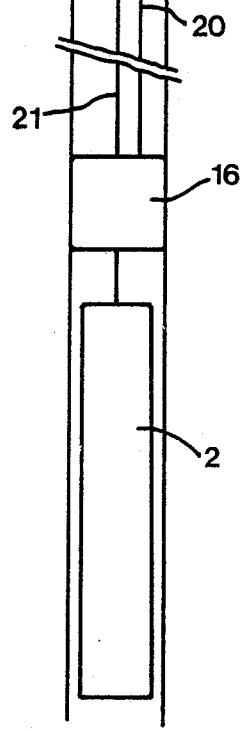
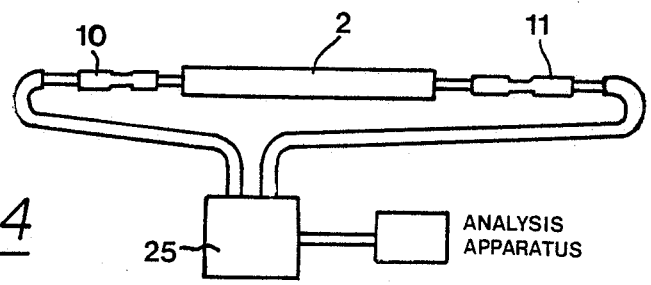
*FIG 2*
*FIG 4*

BOREHOLE SAMPLING

This invention relates to the taking of samples from wells and boreholes. A particular application of the invention is in the taking of water samples from the ground for the purpose of testing the water for contamination.

In the past, the main purpose of sampling was to test for the presence of inorganic contaminants such as nitrates and metals etc. More recently, however, the trend has been towards testing the water also for organic contaminants, such as trichloro-ethane etc. Organic substances tend to have a more highly concentrated effect than inorganic substances, which means that even minute quantities of an organic substance can significantly contaminate the water. It is recognized, in the invention, that testing procedures have to become much more sophisticated if they are to be effective in accurately measuring these minute quantities. Samples that contain organic contaminants are more susceptible to changes during and after sampling.

The invention provides a sampler, sampling apparatus, and a sampling method, which are aimed at making it possible to obtain reliable samples for analysis.

In the invention, the operation of taking and analysing a water sample is carried out in the following manner. First, a sampler is passed into a pre-formed well or borehole to the required depth. The sampler is closed to the water in the borehole at this point. The sampler is opened, and water from the borehole flows into the sampler. The water is retained in a reservoir which is included as part of the sampler. The sampler is preferably sealed into the borehole by means of a packer while the water is being admitted to the sampler.

Next, in the invention, the following procedure is carried out:

(a) the sampler is closed to the entry of any further water;

(b) then the sampler, if sealed, is unsealed from the borehole;

(c) then the sampler is extracted from the borehole;

(d) then the reservoir is sealed off, and detached from the sampler;

(e) then the sealed-off reservoir is despatched to the testing station;

(f) at the testing station the sample is transferred from the reservoir to the analysis apparatus;

(g) and then finally the analysis itself is carried out.

In the invention, the opening and closing of the reservoir preferably is accomplished by providing a check-valve which is set so as to close automatically when the pressure inside the sampler exceeds the pressure outside the sampler. Thus, the check-valve can be closed by pressurising the inside of the sampler to a relatively high pressure. The high pressure can be supplied from outside the borehole. The reservoir in the sampler therefore can be opened to admit a sample, or can be closed, by adjusting the pressure in the sampler. The pressure in the sampler is a parameter that is very easy to adjust and control from outside the borehole, as will become apparent from the ensuing description.

Similarly, the water-sample can be drawn into the reservoir of the sampler simply by reducing the pressure inside the sampler.

In the invention, the sealing of the reservoir—after the sampler has been withdrawn from the borehole—preferably is accomplished by crimping a suitable crimpable portion of the sampler. Thus the ends of the reservoir are pinched off, or crimped, leaving the contents of the reservoir sealed inside. When it is time to analyse the contents, the crimpable portions may be uncrimped, and the sample released into the testing apparatus.

In the invention, the sample may be contained inside the reservoir for long periods with confidence that the sample will not be contaminated from outside the reservoir, nor that any of the sample will be lost. This latter aspect can be important because some of the organic contaminants are volatile. In the invention, the sample can even be protected from deterioration which might occur due to exposure to light, providing the reservoir is made of an opaque material.

The material of the sampler, and particularly of the reservoir, is important from the contamination point of view. The material must of course be watertight. In this respect it should be noted that most plastic materials cannot be relied upon to form an absolute barrier to water and to the contaminants. Over a period of time a transfer of molecules can take place into and through most plastic materials.

The material also should neither release any substance into the sample, nor absorb any substance from the sample. Again, plastics cannot be relied upon.

In the invention, stainless-steel is recognised as one suitable material for the reservoir.

The crimpable portions of the sampler should be of such material and of such dimensions that it is easy for a person to make such a good crimp that sealing is assured. Equally, it is important that the crimpable portion can be uncrimped without difficulty. It is an advantage also if the sampler, after having been crimped and uncrimped, can be re-used. Copper is a suitable material for the crimpable portions, and suitable dimensions are set out below.

DETAILED DESCRIPTION OF THE PREFERRED EMBODIMENT OF THE INVENTION

Further aspects of the invention will become clear from the following description of a sampler which embodies the invention, and of the procedure under which the sampler is used.

In the accompanying drawings:

FIG. 2 is a cross-section of the sampler of FIG. 1, in conjunction with the rest of the apparatus needed to carry out the sampling function;

FIG. 3 is a view of a part of the sampler, which has been detached for transit and storage prior to analysis of the sample;

FIG. 4 is a diagram of the sample being removed from the sampler, prior to analysis.

Figure 1:
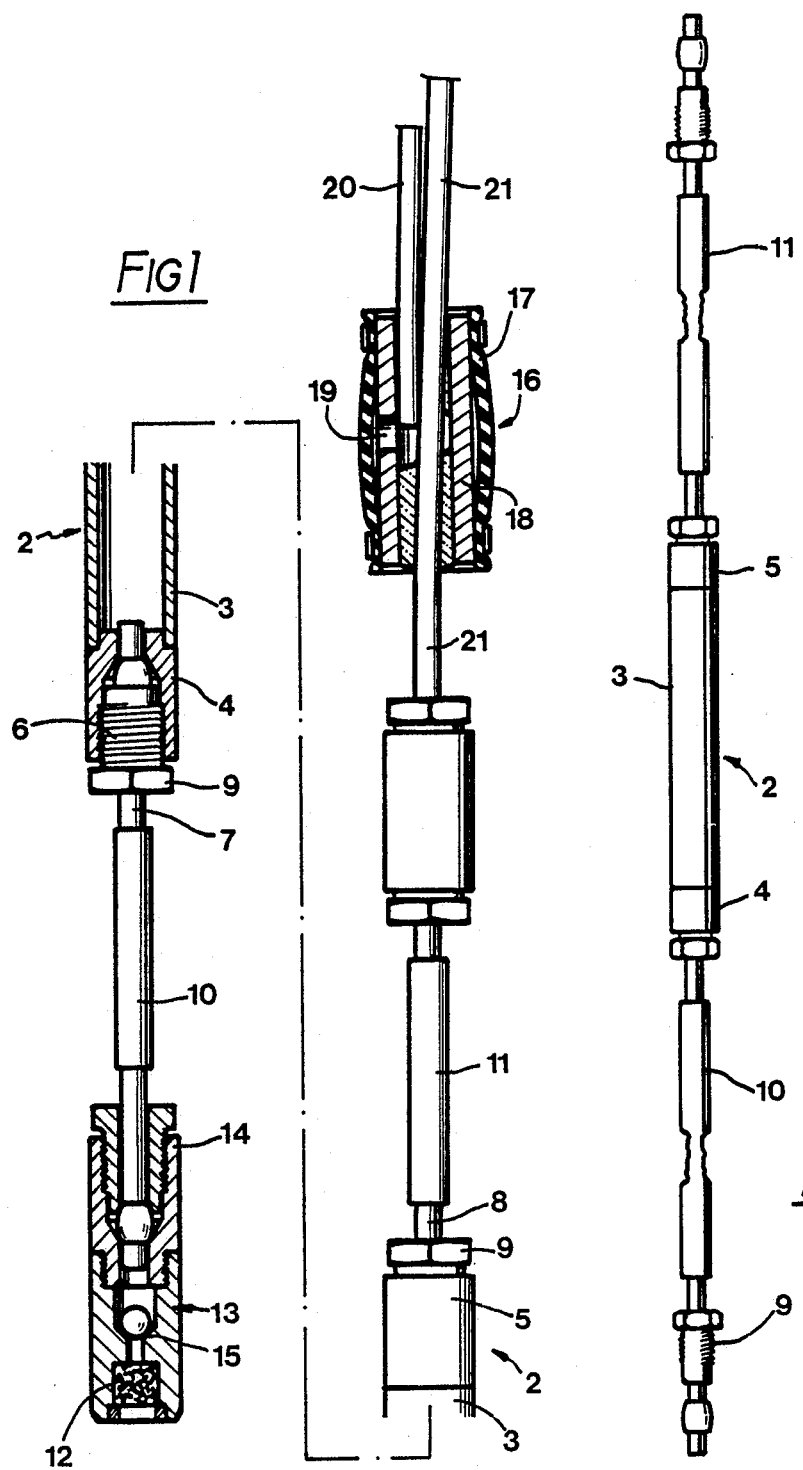
FIG. 1 is a cross-section of the sampler.

The sampler shown in FIG. 1 is suitable for insertion into a borehole of small diameter, for example a diameter of 8 mm. The borehole may be lined with a suitable material—when the borehole is a well, for example, the well may be fitted with a casing in the form of a plastic or steel pipe, at the bottom of which is fitted a screen to admit water—or the borehole may be used directly as-cut if the soil or rock in which it is cut is self-supporting. The borehole itself is not shown in FIG. 1.

The sampler 1 includes a reservoir 2, which is made of stainless steel. The reservoir 2 comprises a tubular middle-portion 3, onto which two end pieces 4, 5 have been secured by a silver-soldering operation. The end-pieces 4, 5 are formed with respective screw-threaded ports 6.

Pipes 7, 8 are secured to the end-pieces 4, 5 respectively by means of pipe-fittings 9. Crimpable portions 10, 11 are brazed to the pipes 7, 8 respectively, the crimpable portions comprising lengths of simple copper tubing. The tubing used in the particular example described was of 1 mm internal diameter, and 3 mm external diameter. The copper was not annealed.

It is recognised in the invention that un-annealed copper of the above dimensions can be readily crimped by a person equipped with a pair of conventional hand-operated crimping pliers. After crimping such a copper tube, the tube remains faithfully sealed during transit and storage.

Attached to the lower crimpable portion 10 is a pre-filter 12 and a check-valve assembly 13, both of which are built into a housing 14. The pre-filter 12 is of a fairly course mesh, its purpose being to prevent gross particles of earth from entering the sampler. The pre-filter 12 is designed to allow particles held in suspension in the water to enter the sampler, since such water-borne particles may be contaminants themselves. The pre-filter 12 may be omitted if not required; if required, the drawings show how readily it may be included.

The check-valve 13 includes a ball-and-seat assembly 15. As may be determined by a perusal of FIG. 1, the assembly 13 is effective to seal off the reservoir 2—both against the entry of more water from the borehole, and against the leakage of water already collected—when the sampler contains a higher pressure than the borehole.

Positioned above the other crimpable portion 11 is an inflatable packer assembly 16. The purpose of the packer 6 is to seal the sampler into the borehole. The packer 6 includes an elastomeric collar 17, which is sealed to a sleeve 18. A hole 19 in the sleeve 18 allows air to act upon the collar, to inflate the collar into contact with the walls of the borehole. Air is fed to the inside of the sleeve 18 through a supply-pipe 20, which leads all the way down the borehole from the ground surface. Thus the operation of the packer 16 can be controlled from the surface, in a similar manner to that of the check-valve 13.

The sleeve 18 fits around a feed-pipe 21, which leads from the top of the upper crimpable portion 11 to the surface.

The use of a sealing packer, such as the one described, is preferred because it ensures that the sample is taken from the correct height in the borehole, and also the use of the packer enables the sampler-to-borehole pressure to be controlled more accurately.

In the particular sampler shown, the feed-pipe 21 that connects the sampler to the surface, and the check-valve 13, are located at the respective opposite ends of the reservoir. While this is a very convenient arrangement, it is not an essential one, in that both could be provided at the same end of the reservoir 2.

Above ground, the sampler is connected to other components as shown in FIG. 2. The particular apparatus shown includes a vacuum source 22 which is coupled to the borehole, and which is effective—upon being actuated—to create a suction at the top of the borehole. The feedpipe 21 and the supply-pipe 20 are connected to respective pressure controllers 23, 24, which allow the pressures in the two pipes to be controlled independently.

The procedure for taking a sample will now be described. First, standing water in the borehole may be extracted, by sucking the water out or by blowing it out, to ensure that the sample is a fresh one—or, the sample may be taken from the standing water if that is desired. Then the sampler is lowered into the borehole and the pipes 20, 21 are connected as shown. Again, the engineer can arrange to flush the water around the sampler by means of the vacuum source 22, if desired.

Next, the packer 13 is inflated by means of the pressure controller 23 and the supply-pipe 20. The inflated packer 13, in addition to sealing the sampler to the borehole, also acts to physically locate the sampler to the borehole.

Up to now, the sampler has been under sufficient internal pressure to keep the check-valve 13 closed. Using the pressure controller 24, the pressure in the sampler is now lowered. The check-valve 13 therefore opens and admits a sample of the water from the borehole into the reservoir 2. The quantity of water drawn in can be controlled by adjusting the pressure in the reservoir: the quantity should be sufficient to fill the reservoir, and to fill the crimpable portion 11 and a little of the feed-pipe 21.

Next, the pressure in the sampler is once again raised, so as to close off the check-valve 13. The packer 16 is deflated, and the sampler is removed from the borehole. The pressure should be maintained in the sampler at this stage, while the sampler is taken out of the borehole or well.

Once the sampler is out of the borehole, the two crimpable portions are crimped. After that, the pressure-controller 24 may be disconnected, and in fact the sampler itself can be detached from the rest of the components of the sampler apparatus, leaving just the reservoir 2 and the two crimped crimpable portions 10, 11 as the container of the sample. This unit (shown in FIG. 3) is easily transported to the laboratory for analysis.

It will be noted from the above description how easy it is, even for a relatively unskilled person, using the invention, to collect and store a sample, and yet the sample is virtually assured of being retained complete and itself uncontaminated.

FIG. 4 shows how the water-sample may be transferred from the reservoir 2 to the analysis apparatus. The two crimpable portions 10, 11 are coupled to a manifold 25, by means of the screw-threaded pipe fittings 9. The crimpable portions may now be uncrimped, which allows the sample to pass into the analysis apparatus.

It is recognised in the invention that crimping such copper tube as that described provides a very convenient manner of sealing-in the sample. Other ways of sealing the reservoir tend to lead to extra diameter of the sampler.

It is, of course, important that the sample can be readily extracted, and again there is no problem with the use of the copper tube in this respect. The tube can be uncrimped by squeezing the crimped area at 90 degrees to the crimp itself. It has been found that the crimpable portions can be crimped and uncrimped several times, the seal being perfect each time. Alternatively the crimpable portions may be long, so that there is room to make fresh crimps at different locations.

Sometimes, it may be preferred to reinforce the crimped seal during transit and storage, in which case a simple screw clamp can be fitted around the copper tube. The clamp is not present while the sampler is down the borehole, so that the diametral size of the clamp need not be constrained. It is possible indeed for the copper to be replaced with a material that will not seal when crimped—an elastomeric material for example. A clamp of some kind is therefore then essential, which must be set while the sampler is still under pressure, and which must be left on during transit. However, the use of nonmetals in the sampler is not preferred, since such use can lead to the disadvantages mentioned.

Vacuum and/or pressure may be used to force the sample to flow into the analysis apparatus in the desired manner, though the arrangement should be such that gases contained in with the water sample are retained also for the analysis.

An important aspect of the invention is that a sample can be retained in the sampler at the very pressure the sample was at in the borehole. It can even be arranged that the sample is kept at that pressure during the transfer to the analysis apparatus, and during the analysis itself. This aspect is useful where the gaseous content of the sample is to be included in the analysis.

Another important criterion in the design of a sampler is that the sampler be small as regards its outer diameter. The sampler described above can be extremely slim and able to pass down the narrowest of boreholes or wells.

After use, the sampler and the rest of the sampling apparatus should be throughly cleaned and made ready for re-use. It will be noted that the sampler itself is of a relatively inexpensive construction, so that one-time-use only can be economically feasible in critical cases. The use of stainless steel in the construction of the sampler is, on the other hand, conducive to easy cleaning. The sampler could even be responsible itself for introducing a contaminant into a borehole, if the sampler is not properly cleaned.

We claim:

1. Sampler, which is suitable for use in and with apparatus for collecting a sample of liquid from a deep borehole, wherein:
    the sampler includes a sample-collection-reservoir, which is suitable for containing a sample of the liquid, and which is adapted for lowering into the borehole;
    the reservoir is provided with a remotely operable check valve means, and a directly operable sealing means, both of which are operable between a respective open condition and a respective closed condition;
    when in the open condition the means are effective to allow liquid to enter and leave the reservoir and when in the closed condition the means are effective to prevent liquid from entering or leaving the reservoir;
    the apparatus includes a means for supplying a check valve control pressure from above ground, remote from the reservoir and sealing means, and outside the borehole;
    the sampler includes a means for conducting the said pressure to check valve means when the reservoir is within the borehole;
    the sampler includes a means responsive to the said applied pressure supplied from above ground, for operating the check valve means between the said open and closed conditions;
    the sampler includes a means for operating the sealing means directly manually;
    and the arrangement of the sampler is such that the means for operating the sealing means is accessible for direct manual operation when the sampler is outside the borehole.

2. Sampler of claim 1, where the said sealing means comprises a length of tubing, which is of such material and dimensions that the tubing may be crimped by the use of a crimping means, and may be crimped to such an extent that the tubing becomes impassable to the passage of fluids.

3. Sampler of claim 2, where the material of the tubing is copper.

4. Sampler of claim 3, where the tubing has an internal diameter of 1 mm, and an external diameter of 3 mm.

5. Method of extracting samples of liquid from a deep borehole, comprising the steps:
    of providing the sampler of claim 1;
    of providing a check-valve in the or in one of the pipes, the check-valve being so arranged as to be open for the conduction of fluid along the pipe when the pressure in the reservoir is less than the pressure in the borehole, and as to be closed to the conduction of fluid along the pipe when the pressure in the reservoir is more than the pressure in the borehole;
    of pressurising the reservoir with sufficient pressure to keep the check-valve closed;
    of then reducing the pressure in the reservoir to a low enough value to open the check-valve and to permit liquid from the borehole to enter the reservoir;
    of then increasing the reservoir pressure to a high enough value to keep the check-valve closed;
    of then extracting the sampler from the borehole;
    of then closing the said sealing means;
    and of then detaching the sampler from the rest of the apparatus.

6. Method of claim 5, comprising the further steps:
    of providing a packer which is suitable, upon being operated, for sealing the reservoir in the borehole;
    and of operating the packer after inserting the sampler in the borehole but before reducing the pressure in the reservoir;
    and of de-operating the packer after increasing the pressure in the reservoir but before extracting the sampler.

7. Apparatus for extracting a liquid sample from a deep borehole, comprising:
    the sampler of claim 1;
    a check-valve being so arranged as to be open for the conduction of fluid along the pipe when the pressure in the reservoir is less than the pressure in the borehole, and as to be closed to the conduction of fluid along the pipe when the pressure in the reservoir is more than the pressure in the borehole;
    and means for changing the pressure inside the reservoir.

8. Apparatus of claim 7, further comprising:
    a packer, which is effective when operated to seal the sampler into the borehole;
    and means for operating the packer.

9. Apparatus of claim 8, where the packer comprises a flexible collar, which is operated by being inflated.

10. Apparatus of claim 7, where the sealing means is located between the reservoir and the check-valve.

11. Sampler of claim 1, wherein:
    a main body of the reservoir is of elongate right tubular form;

the sealing means comprises an upper sealing means and a lower sealing means, which are located respectively at the upper and lower ends of the body;

the check valve means is located at the lower end of the body, and below the lower sealing means;

the reservoir includes a coupling means, for attaching to the reservoir the means for conducting pressure to the reservoir;

the coupling means is located at the upper end of the body, and above the upper sealing means;

and the reservoir includes a means for detaching the coupling means from the reservoir, in such a manner that when the coupling means is detached the sealing means remains manually operable.

12. Sampler of claim 11, wherein the reservoir includes a means for detaching the check valve means from the reservoir, in such a manner when the check valve means is detached the sealing means remains manually operable.

13. Sampler of claim 12, where the means for detaching the coupling means from the reservoir, and the means for detaching the check valve means from the reservoir, comprise screw-together pipe-fittings.

14. Method of extracting a sample from a deep borehole, comprising the steps:

of providing the sampler of claim 12;

before lowering the sampler into the borehole, of manually operating the upper and lower sealing means to the open condition, and of applying pressure to operate the check valve to the closed position;

of lowering the reservoir into the borehole to the depth at which the sample is to be taken;

of adjusting the applied pressure so as to operate the check valve to the open condition;

of allowing enough time for the sample to enter the reservoir;

of adjusting the applied pressure so as to operate the check valve back to the closed condition;

of withdrawing the reservoir from the borehole;

of manually operating the upper and lower sealing means to the closed condition, thereby sealing the reservoir;

and, when the reservoir is sealed, of detaching the coupling means and the check valve means from the reservoir.

15. Method of extracting a sample of a liquid from a deep borehole, comprising the steps of:

providing the sampler of claim 1;

while the sampler is outside the borehole, operating the said sealing means, directly manually, to the open condition, and operating the check valve means to the closed position by applying the said check valve control pressure;

lowering the reservoir down the borehole to the depth at which the sample is to be taken;

operating the check valve to the open condition by means of the check valve control pressure;

when the sample has entered the reservoir, operating the check valve to the closed condition;

raising the reservoir out of the borehole;

and then operating the sealing means to the closed condition.

* * * * *